(12) United States Patent
Loesener (10) Patent No.: US 10,272,227 B2
(45) Date of Patent: Apr. 30, 2019

(54) CONNECTION SYSTEM FOR TUNNELED CATHETERS

(71) Applicant: C. R. Bard, Inc., Murray Hill, NJ (US)

(72) Inventor: German Loesener, Riverton, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 217 days.

(21) Appl. No.: 14/935,364

(22) Filed: Nov. 6, 2015

(65) Prior Publication Data

US 2016/0129222 A1    May 12, 2016

Related U.S. Application Data

(60) Provisional application No. 62/077,130, filed on Nov. 7, 2014.

(51) Int. Cl.
*A61M 25/00* (2006.01)
*A61M 25/01* (2006.01)
(Continued)

(52) U.S. Cl.
CPC ........ *A61M 25/0097* (2013.01); *A61M 1/285* (2013.01); *A61M 25/0009* (2013.01);
(Continued)

(58) Field of Classification Search
CPC ................. A61M 25/0014; A61M 2025/0031
(Continued)

(56) References Cited

U.S. PATENT DOCUMENTS 3,879,516 A * 4/1975 Wolvek ............ A61M 25/0012
264/135
4,385,631 A   5/1983 Uthmann
(Continued)

FOREIGN PATENT DOCUMENTS

GB     1503469       3/1978
WO   01/97743 A2   12/2001
(Continued)

OTHER PUBLICATIONS

STIC Search, dated Dec. 8, 2017. 3 documents.*
(Continued)

*Primary Examiner* — Nathan R Price
*Assistant Examiner* — John A Doubrava
(74) *Attorney, Agent, or Firm* — Rutan & Tucker, LLP (57) ABSTRACT

A catheter assembly is disclosed, comprising a proximal catheter assembly portion and a distal catheter assembly portion. The proximal catheter assembly portion includes a bifurcating hub that defines at least one fluid passageway. The distal catheter assembly portion includes a catheter tube that defines at least one lumen and includes a polymeric material. A cannula assembly is also disclosed and includes at least one cannula that is operably connected with the fluid passageway of the birfurcating hub. The cannula is further configured to operably connect with the lumen of the catheter tube so as to provide fluid communication between the proximal and distal catheter assembly portions when the two portions are connected. A polymeric coating is included with the cannula and the catheter tube, and is configured to provide a seal between the cannula and the catheter tube when the proximal and distal catheter assembly portions are connected together.

30 Claims, 8 Drawing Sheets

(51) Int. Cl.
*A61M 1/28* (2006.01)
*A61M 39/10* (2006.01)
*A61M 39/12* (2006.01)
*A61M 25/02* (2006.01)
*A61M 1/36* (2006.01)

(52) U.S. Cl.
CPC ...... *A61M 25/0194* (2013.01); *A61M 39/105* (2013.01); *A61M 39/12* (2013.01); *A61M 1/3661* (2014.02); *A61M 2025/0006* (2013.01); *A61M 2025/0293* (2013.01)

(58) Field of Classification Search
USPC ...................................... 604/537; 264/171.26
See application file for complete search history.

(56) References Cited

U.S. PATENT DOCUMENTS

| | | | |
|---|---|---|---|
| 4,405,313 A | 9/1983 | Sisley et al. | |
| 4,431,426 A | 2/1984 | Groshong et al. | |
| 4,453,928 A | 6/1984 | Steiger | |
| 4,583,968 A | 4/1986 | Mahurkar | |
| 4,619,643 A | 10/1986 | Bai | |
| 4,776,841 A | 10/1988 | Catalano | |
| 4,832,687 A | 5/1989 | Smith, III | |
| 4,906,237 A * | 3/1990 | Johansson | A61L 29/14 604/265 |
| 4,936,826 A | 6/1990 | Amarasinghe | |
| 4,950,255 A | 8/1990 | Brown et al. | |
| 5,009,636 A | 4/1991 | Wortley et al. | |
| 5,053,023 A | 10/1991 | Martin | |
| 5,057,073 A | 10/1991 | Martin | |
| 5,188,593 A | 2/1993 | Martin | |
| 5,190,520 A * | 3/1993 | Fenton, Jr. | A61M 25/005 604/43 |
| 5,190,529 A | 3/1993 | McCrory et al. | |
| 5,221,255 A | 6/1993 | Mahurkar et al. | |
| 5,234,438 A | 8/1993 | Semrad | |
| 5,306,240 A | 4/1994 | Berry | |
| 5,380,276 A | 1/1995 | Miller et al. | |
| 5,389,090 A | 2/1995 | Fischell et al. | |
| 5,405,320 A | 4/1995 | Twardowski et al. | |
| 5,405,341 A | 4/1995 | Martin | |
| 5,431,661 A | 7/1995 | Koch | |
| 5,509,897 A | 4/1996 | Twardowski et al. | |
| 5,685,867 A | 11/1997 | Twardowski et al. | |
| 5,718,678 A | 2/1998 | Fleming, III | |
| 5,858,009 A | 1/1999 | Jonkman | |
| 5,944,732 A | 8/1999 | Raulerson et al. | |
| 5,961,486 A | 10/1999 | Twardowski et al. | |
| 5,989,206 A | 11/1999 | Prosl et al. | |
| 6,146,371 A | 11/2000 | DeWindt et al. | |
| 6,375,648 B1 | 4/2002 | Edelman et al. | |
| 6,453,185 B1 | 9/2002 | O'Keefe | |
| 6,461,321 B1 | 10/2002 | Quinn | |
| 6,475,244 B2 | 11/2002 | Herweck et al. | |
| 6,517,529 B1 | 2/2003 | Quinn | |
| 6,533,763 B1 | 3/2003 | Schneiter | |
| 6,565,594 B1 | 5/2003 | Herweck et al. | |
| 6,592,544 B1 | 7/2003 | Mooney et al. | |
| 6,638,242 B2 | 10/2003 | Wilson et al. | 604/43 |
| 6,702,776 B2 | 3/2004 | Quinn | |
| 6,719,749 B1 | 4/2004 | Schweikert et al. | |
| 6,749,574 B2 | 6/2004 | O'Keefe | |
| 6,752,827 B2 | 6/2004 | Ross et al. | |
| 6,858,019 B2 | 2/2005 | McGuckin, Jr. et al. | |
| 6,872,198 B1 | 3/2005 | Wilson et al. | |
| 6,916,313 B2 | 7/2005 | Cunningham | |
| 6,921,396 B1 | 7/2005 | Wilson et al. | |
| 7,018,384 B2 | 3/2006 | Skakoon | |
| 7,108,674 B2 | 9/2006 | Quinn | |
| 7,128,734 B1 | 10/2006 | Wilson et al. | |
| 7,141,035 B2 | 11/2006 | Haggstrom | |
| 7,182,746 B2 | 2/2007 | Haarala et al. | |
| D542,414 S | 5/2007 | Atkins | |
| 7,258,685 B2 | 8/2007 | Kerr | |
| 7,276,055 B2 | 10/2007 | DeWindt et al. | |
| 7,300,430 B2 | 11/2007 | Wilson et al. | |
| 7,381,204 B2 | 6/2008 | Wilson et al. | |
| 7,390,322 B2 | 6/2008 | McGuckin, Jr. et al. | |
| 7,566,316 B2 | 7/2009 | McGuckin, Jr. et al. | |
| 7,569,029 B2 | 8/2009 | Clark | |
| 7,628,795 B2 | 12/2009 | Karwoski et al. | |
| 7,731,708 B2 * | 6/2010 | Haarala | A61M 25/0097 604/534 |
| 7,740,616 B2 | 6/2010 | Smith et al. | |
| 7,749,185 B2 | 7/2010 | Wilson et al. | |
| 7,753,868 B2 | 7/2010 | Hoffa | |
| 7,776,005 B2 | 8/2010 | Haggstrom et al. | |
| 7,806,889 B2 | 10/2010 | Raulerson et al. | |
| 7,833,214 B2 | 11/2010 | Wilson et al. | |
| 7,875,019 B2 * | 1/2011 | Barron | A61M 25/0014 604/534 |
| 7,914,513 B2 | 3/2011 | Voorhees, Jr. | |
| 7,988,658 B2 | 8/2011 | Quinn | |
| 8,100,884 B2 | 1/2012 | Schweikert et al. | |
| 8,105,313 B2 | 1/2012 | Schweikert et al. | |
| 8,137,316 B2 | 3/2012 | Haarala et al. | |
| 8,167,867 B2 | 5/2012 | Briscoe et al. | |
| 8,251,975 B2 | 8/2012 | Atkins et al. | |
| 8,361,011 B2 | 1/2013 | Mendels | |
| 8,454,565 B2 | 6/2013 | Braga et al. | |
| 8,496,607 B2 | 7/2013 | Feng et al. | |
| 8,500,674 B2 | 8/2013 | DeFonzo et al. | |
| 8,518,013 B2 | 8/2013 | Kurrus et al. | |
| 8,603,067 B2 | 12/2013 | Lareau et al. | |
| 8,852,168 B2 | 10/2014 | Barron et al. | |
| 8,905,998 B2 | 12/2014 | Stephens | |
| 9,242,071 B2 | 1/2016 | Morgan et al. | |
| 2001/0020160 A1 * | 9/2001 | Esch | A61B 17/12109 604/509 |
| 2003/0088213 A1 | 5/2003 | Schweikert et al. | |
| 2003/0135197 A1 | 7/2003 | Wang et al. | |
| 2004/0172003 A1 | 9/2004 | Wilson et al. | |
| 2004/0176739 A1 | 9/2004 | Stephens et al. | |
| 2004/0193119 A1 | 9/2004 | Canaud et al. | |
| 2004/0210237 A1 | 10/2004 | Ross et al. | |
| 2004/0230204 A1 | 11/2004 | Wortley et al. | |
| 2005/0027282 A1 | 2/2005 | Schweikert et al. | |
| 2005/0228364 A1 | 10/2005 | Braga | |
| 2005/0261636 A1 | 11/2005 | Rome et al. | |
| 2006/0009783 A1 | 1/2006 | Rome et al. | |
| 2006/0015130 A1 | 1/2006 | Voorhees et al. | |
| 2006/0095062 A1 | 5/2006 | Stephens | |
| 2006/0100572 A1 | 5/2006 | DiMatteo et al. | |
| 2007/0049960 A1 | 3/2007 | Stephens et al. | |
| 2007/0066964 A1 | 3/2007 | Atkins | |
| 2007/0078396 A1 | 4/2007 | Feeley et al. | |
| 2007/0078478 A1 | 4/2007 | Atkins et al. | |
| 2007/0265597 A1 | 11/2007 | Schweikert et al. | |
| 2007/0282274 A1 | 12/2007 | Chesnin | |
| 2008/0032611 A1 * | 2/2008 | Dilyard | B24D 11/00 451/344 |
| 2008/0097409 A1 | 4/2008 | Stephens | |
| 2008/0214992 A1 | 9/2008 | Haarala et al. | |
| 2009/0030426 A1 | 1/2009 | Zinn et al. | |
| 2009/0088699 A1 | 4/2009 | King et al. | |
| 2009/0137944 A1 * | 5/2009 | Haarala | A61M 25/0194 604/44 |
| 2009/0148591 A1 | 6/2009 | Wang et al. | |
| 2009/0187141 A1 | 7/2009 | Lareau et al. | |
| 2009/0221950 A1 | 9/2009 | Atkins | |
| 2009/0247927 A1 | 10/2009 | Clark | |
| 2009/0299377 A1 | 12/2009 | Bright | |
| 2010/0063512 A1 | 3/2010 | Braga et al. | |
| 2010/0063513 A1 | 3/2010 | Braga et al. | |
| 2010/0069950 A1 | 3/2010 | Rabbitte et al. | |
| 2010/0168642 A1 | 7/2010 | Appling et al. | |
| 2010/0174183 A1 | 7/2010 | Schwartz et al. | |
| 2010/0174291 A1 | 7/2010 | Atkins et al. | |
| 2011/0098653 A1 * | 4/2011 | Powers | A61M 25/0014 604/174 |
| 2011/0213291 A1 | 9/2011 | Quinn | |

(56) References Cited

U.S. PATENT DOCUMENTS

| | | |
|---|---|---|
| 2012/0016285 A1 | 1/2012 | Contractor |
| 2012/0083766 A1* | 4/2012 | Haarala ............. A61M 25/0097 604/539 |
| 2012/0148175 A1 | 6/2012 | Wesselmann |
| 2012/0209221 A1 | 8/2012 | Patterson et al. |
| 2013/0245568 A1* | 9/2013 | Kerr ........................ A61L 29/06 604/264 |
| 2014/0155801 A1 | 6/2014 | Zinn et al. |
| 2014/0358120 A1 | 12/2014 | Haarala et al. |
| 2015/0051536 A1 | 2/2015 | Mendels et al. |
| 2015/0320927 A1 | 11/2015 | Nardeo |
| 2016/0067472 A1 | 3/2016 | Haarala et al. |

FOREIGN PATENT DOCUMENTS

| | | |
|---|---|---|
| WO | 2009015016 A1 | 1/2009 |
| WO | 2016/073954 A1 | 5/2016 |

OTHER PUBLICATIONS

Web Page Screen Shot—Adhesiveandglue.com from Jul. 3, 2018—Elastomer—examples.*
PCT/US2015/059620 filed Nov. 6, 2015 International Search Report and Written Opinion dated Jan. 28, 2016.
EP 15856731.3 filed Jun. 6, 2017 Extended European Search Report dated May 25, 2018.

* cited by examiner

CONNECTION SYSTEM FOR TUNNELED CATHETERS

CROSS-REFERENCE TO RELATED APPLICATIONS

This application claims the benefit of U.S. Provisional Application No. 62/077,130, filed Nov. 7, 2014, and titled "Connection System for Tunneled Catheters," which is incorporated herein by reference in its entirety.

BRIEF SUMMARY

Briefly summarized, embodiments of the present invention are directed to a catheter for use in providing access to a vessel or other internal portion of a body of a patient. In one embodiment, the catheter is a dialysis catheter that includes initially separate proximal and distal catheter assembly portions to enable the catheter to be tunneled before connecting the two catheter assembly portions together. In particular, the embodiments herein describe a system for connecting the catheter assembly together such that the resultant assembly provides a leak-proof catheter.

The embodiments described herein are applicable to catheters that are inserted in a retrograde, or reverse tunneling, procedure, which procedure requires assembly of the catheter after the tunneling procedure has been performed. Such reverse-tunneled catheter assemblies are typically employed as acute or chronic dialysis catheters, central venous catheters ("CVCs"), etc., though it is appreciated that a variety of catheter assemblies and tubular medical devices disposed within the patient body can benefit from the teachings herein.

In one embodiment, a catheter assembly is disclosed that comprises a proximal catheter assembly portion and a distal catheter assembly portion. The proximal catheter assembly portion includes a bifurcating hub that defines at least one fluid passageway. The distal catheter assembly portion includes a catheter tube that defines at least one lumen, with the catheter tube including a polymeric material. A cannula assembly is also disclosed and includes at least one cannula that is operably connected with the fluid passageway of the birfurcating hub. The cannula is further configured to operably connect with the lumen of the catheter tube so as to provide fluid communication between the proximal catheter assembly portion and the distal catheter assembly portion when the two portions are connected.

A polymeric coating is included with the cannula and the catheter tube. The polymeric coating is configured to provide a seal between the cannula and the catheter tube when the proximal catheter assembly portion and the distal catheter assembly portion are connected. Catheters having one, two, or more lumens can benefit from the disclosure discussed herein.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A-2 depict various views of a catheter assembly according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having" as used herein, including the claims, shall have the same meaning as the word "comprising." Further, the words "at least one" as used herein, including the claims, shall be understood to include "one or more" in number.

Embodiments of the present invention are generally directed to a catheter assembly for use in providing access to a vessel or other internal portion of a body of a patient. In particular, the embodiments herein describe a system for connecting the catheter assembly together such that the resultant assembly provides a leak-proof catheter. The embodiments described herein are applicable to catheters that are inserted in a retrograde, or reverse tunneling, procedure, which procedure requires assembly of the catheter after the tunneling procedure has been performed. Such reverse-tunneled catheter assemblies are typically employed as acute or chronic dialysis catheters, central venous catheters ("CVCs"), etc., though it is appreciated that a variety of catheter assemblies and tubular medical devices disposed within the patient body can benefit from the teachings herein.

Figure 1A:
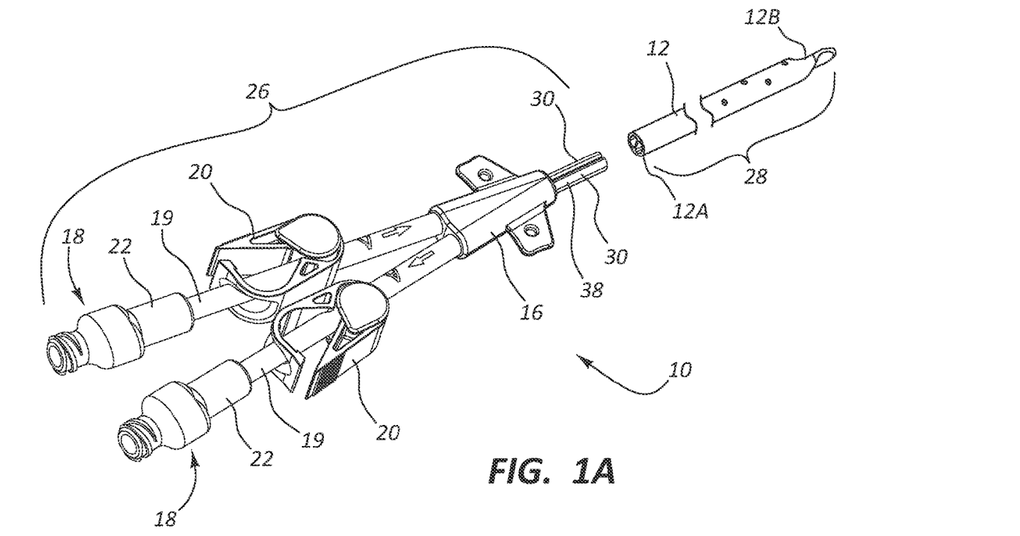
Figure 1B:
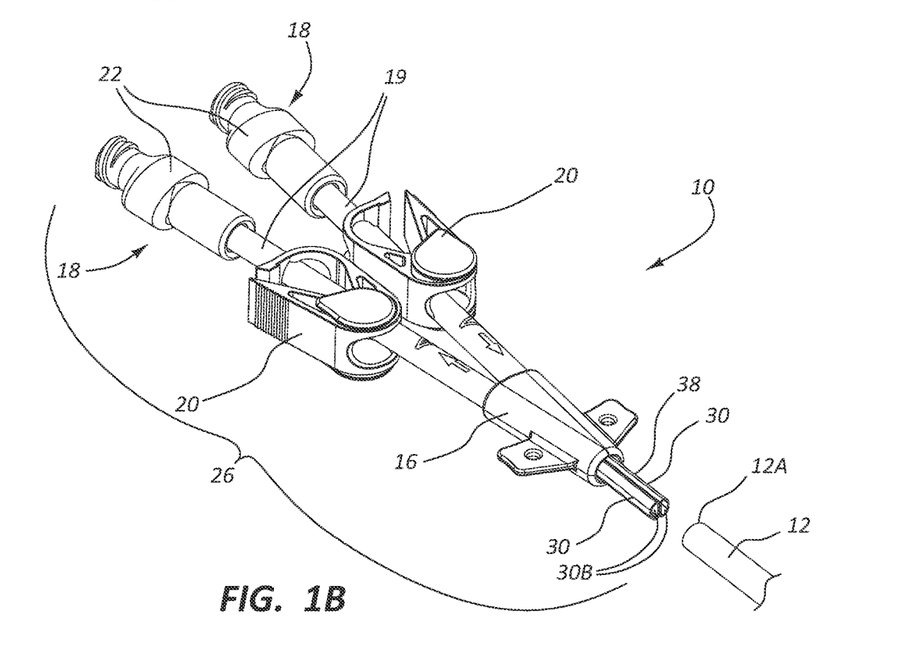
Figure 2:
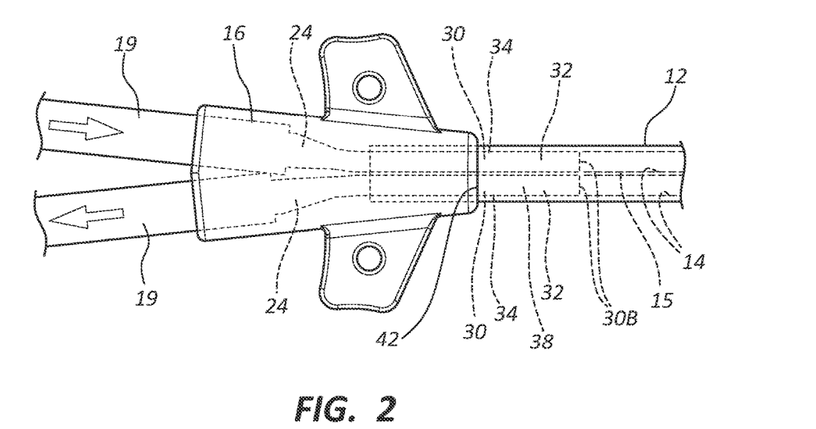

Reference is first made to FIGS. 1A-2, which depict details of a catheter assembly ("catheter"), generally designated at 10, according to one embodiment. As shown, the catheter 10 includes a catheter tube 12 defining two lumens 14 that extend between a proximal end 12A and a distal end 12B of the catheter tube. A septum 15 longitudinally extends within the catheter tube 12 to separate the lumens 14. Note that fewer or more lumens can be defined by the catheter tube. Note also that, though shown here as a dialysis catheter, the catheter assembly can include one of a variety of types of catheters or tubular medical devices for disposal in the body of the patient. In one embodiment, the catheter 10 is a dialysis catheter of 14.5 French size, though other sizes of catheters are also possible.

A proximal end 12A of the catheter tube 12 is configured for operable attachment to a bifurcation hub 16 that provides fluid communication between each of the lumens 14 of the catheter tube and a corresponding one of extension legs 18, also operably attached to the bifurcation hub 16. As the catheter tube 12 of the present embodiment includes two lumens 14, two extension legs 18 are included with the catheter 10 and the bifurcation hub 16 correspondingly provides two internal fluid passageways 24 (FIG. 2) for operable connection of the lumens and corresponding extension legs. Each extension leg 18 includes an extension tube 19 through which fluid can flow to/from the bifurcation hub 16 and corresponding catheter tube lumen 14, a clamp 20, and a connector 22. The number of extension legs can vary from what is shown and described herein.

FIGS. 1A and 1B further show that the catheter 10 includes a proximal catheter assembly portion 26, which in the present embodiment includes the bifurcation hub 16 and extension legs 18, and a distal catheter assembly portion 28, which in the present embodiment includes the catheter tube 12. It is appreciated that the proximal and distal catheter assembly portions 26 and 28 can vary from what is shown in the present embodiment, as will be described.

In the present embodiment, two cannulae 30, also referred to herein as a cannula assembly, are permanently attached to and extend from a distal end of the bifurcation hub 16, best seen in FIG. 1B, and as such are included with the proximal catheter assembly portion 26 in the illustrated embodiment. The cannulae 30 are each configured to be received through the catheter tube proximal end 12A of the distal catheter assembly portion 28 and into a corresponding one of the lumens 14, so as to operably connect the bifurcation hub with the lumens, thus establishing fluid communication therebetween and with the corresponding extension legs 18.

Each cannula 30 includes an outer surface 34 that defines a cannula lumen 32. The cannula lumen 32 extends between a proximal end 30A and a distal end 30B of the respective cannula 30. The outer surface 34 of each cannula 30 is shaped and sized so as to fit into a proximal portion of one of the correspondingly shaped lumens 14 of the catheter tube 12 in an interference-type fit. For instance, in the present embodiment, each of the cannulae 30 defines a generally semi-circular cross sectional lumen shape, matching the semi-circular shape of the catheter tube lumens 14. Each cannula 30 further includes an inner surface 36. In another embodiment, a non-interference, slip-type fit is used for the cannula-to-catheter tube lumen connection. In this case, a compression component can be employed to assist in securing the connection.

As mentioned, though here the outer surface 34 of each cannula 30 defines a generally semi-circular cross-sectionally shaped lumen 32, other cross sectional cannula lumen shapes and numbers are possible to correspond with the lumen(s) of the catheter tube, including round, square, oval, etc. The cannulae 30 include a suitable material, including stainless steel or other metal, thermoplastics, etc. The cannulae 30 can be insert-molded into the body of the bifurcation hub 16 during manufacture thereof, or by other suitable processes.

FIG. 2 shows the manner of attachment between the cannulae 30 (of the proximal catheter assembly portion 26) and the lumens 14 of the catheter tube 12 (of the distal catheter assembly portion 28), where the cannulae are inserted past the proximal end 12A of the catheter tube until the catheter tube proximal end seats against the distal end of the bifurcation hub 16. This connection is referred to herein as a cannulae/catheter tube interface 42. The cannulae outer surfaces 34 and the lumens 14 of the catheter tube 12 are sized so as to provide, in the present embodiment, an interference fit therebetween in the present embodiment so as to assist in providing a leak-free interface. The relative length, size, and configuration of the cannulae 30 can vary from what is shown and described herein. Further details regarding cannulae-equipped bifurcation hubs can be found in U.S. Pat. No. 7,875,019, entitled "Connection System for Multi-Lumen Catheter," which is incorporated herein by reference in its entirety.

In one example implementation, the catheter 10 is a chronic dialysis catheter and is provided to the clinician prior to use with the proximal catheter assembly portion 26 physically separate from the distal catheter assembly portion 28. This enables the clinician to insert the distal segment of the distal catheter assembly portion 28 into the vasculature of the patient, then subcutaneously tunnel the proximal segment of the distal catheter assembly portion such that the proximal end 12A of the catheter tube 12 is exposed atop the skin surface. The proximal catheter assembly portion 28 can then be attached to the proximal end 12A of the catheter 12 via the cannulae 30 to produce the cannulae/catheter tube interface 42 and complete the catheter assembly 10. The catheter assembly 10 can then be dressed and prepared for use. Tunneling of the distal catheter assembly portion 28 before attaching the proximal catheter assembly portion 26 enables the clinician to trim the catheter tube 12 of the distal catheter assembly portion to a desired length before completing catheter assembly.

In accordance with the present embodiment, the cannulae/catheter tube interface 42 is configured so as to substantially prevent leakage therefrom after the above-described assembly of the catheter and use thereof. In particular, a polymeric coating is applied at the cannulae/catheter tube interface 42 to form a fluid-tight interface between the cannulae 30 and the catheter tube 12. This in turn prevents leakage from the cannulae/catheter tube interface 42 even when the catheter 10 is under pressure, such as during fluid infusion into the patient body via the catheter.

In light of the above, in the present embodiment the outer surfaces 34 of both cannulae 30 are coated with a polymeric coating ("coating") 38 to enable a leak-free connection to be established between the cannulae and the catheter tube 12 when joined together, as has been described above. In the present embodiment, the coating 38 for the outer surface 34 of the cannulae 30 includes a material that is substantially chemically similar to that included in the catheter tube 12 itself. For instance, in the present embodiment the catheter tube 12 includes polyurethane and the coating 38 is formed from polyurethane as well.

The use of a coating that is chemically similar to the material included in the catheter tube 12 enables the catheter tube to knit with the coating on the outer surface 34 of the cannulae 30 when the cannulae are inserted into the catheter tube lumens 14 as described above in connection with a dialysis catheter placement for instance. This serves as a seal and helps to provide a leak-free interface between the cannulae 30 and the catheter tube 12, even when creep of the polymeric catheter tube material occurs over time. As used herein, "seal" is understood to include an engagement that prevents the passage of fluid therethrough.

In one embodiment, a polyurethane or other urethane-based coating is used with a polyurethane or other urethane-based catheter tube. In another embodiment, a silicone coating is used with a silicone catheter tube. Other material combinations are also possible, as appreciated by one skilled in the art, including various polymer coatings for use with catheter tubes of various polymers. The coating 38 can be applied to the cannulae 30 or other component via one of various procedures, including dipping, spraying, painting, deposition, extruding, insert molding, etc.

In one embodiment, the outer surfaces 34 of the cannulae 30 can be bead blasted prior to application of the coating 28 to provide surface features on a high surface-area finish and improve coating adhesion. Other methods for providing a roughened or high surface-area finish to the cannula surface to be coated can also be employed, including metal sputtering on the cannula surface, acid etching, etc.

In one example, the composition of the polymeric coating 38 was prepared by dissolving polyurethane pieces into about 6 mL of a solvent, such as tetrahydrofuran ("THF"), in a beaker to form the coating as a polyurethane slurry. The polyurethane pieces were cut from a one-inch portion into slices of thickness from about 0.005 inch to about 0.010 inch. The solvent and polyurethane were mixed until dissolving of the pieces was complete. The outer surfaces of two cannulae were bead blasted with 24 grit aluminum oxide media at 60 p.s.i. for about 15 to about 17 seconds to provide a medium coarse finish on the cannulae surfaces. The polyurethane slurry was then applied to the outer surfaces of two cannulae to define the coating thereon. The thickness of the coating on the outer surfaces of the cannulae was from about 0.0045 inch to about 0.005 inch, though other coating thicknesses are, of course, possible.

In another embodiment, the coating 38 is chemically dissimilar to the material included in the catheter tube 12, in contrast to the previous embodiment. Such chemically dissimilar coatings can also enhance the cannulae/catheter tube interface 42 and seal the interface such that leaking is prevented. For instance, a silicone coating 38 can be applied to the cannulae 30 or other location to seal with a polyurethane catheter tube 12, in one embodiment. In another embodiment, a polyurethane coating 38 can be employed to seal with a silicone catheter tube 12. These and other examples are therefore contemplated.

Note that, in one embodiment, the coating 38 can be applied to the interior walls of the catheter tube lumens 14 in addition to or instead of to the outer surfaces 34 of the cannulae 30. In another embodiment, the cannulae 30 can be configured to fit over the outer perimeter of the catheter tube 12 instead of being received within the lumens thereof In this case, the coating 38 can be applied to the inner surface 36 of the cannulae 30, the outer surface of the catheter tube 12 proximate the proximal end 12A thereof, or both surfaces, in one embodiment. As such, various different sealing configurations employing the coating 38 are contemplated.

Note that the present disclosure contemplates that two chemically similar materials, in one embodiment, each include at least one common polymer, including copolymers and homopolymers, either alone or in combination with other materials so as to be capable of knitting together, or creating a chemical bond and a sealing function, when the materials are placed in intimate contact. Additionally, the present disclosure contemplates that, in one embodiment, chemically dissimilar materials do not share a common polymer such that the materials do not readily bond to one another in intimate contact but are still able to provide a sealing function.

In one embodiment, therefore, the material included in the coating 38 for coating a surface of the cannula and/or catheter tube 12 (or other component to be sealed) can include one or more of the following (non-limiting): polyurethane ("PUR or PU"), silicone ("SI"), polyester ("PES"), polyethyleneterephthalate ("PET"), polyethylene ("PE"), high density polyethylene ("HDPE"), polyvinylchloride ("PVC"), low-density polyethylene ("LDPE"), polypropylene ("PP"), polystyrene ("PS"), polyamides ("PA"), nylons, acrylonitrilebutadiene styrene ("ABS"), polycarbonate ("PC"), polycarbonate/acrylonitrile butadienestyrene ("PC/ABS"), polyetheretherketone ("PEEK"), and polytetrafluoroethylene ("PTFE"). Also, note that any of these materials can be used in any arrangement or combination within themselves or with another polymer, including copolymers and homopolymers. Also, in one embodiment the above materials can include additives and fillers for improved mutual bonding and mechanical properties. Note that the above-noted materials can also be included in the catheter tube 12 as well.

In light of the above, a method of manufacture of the catheter 10 in one embodiment includes providing a proximal catheter assembly portion, such as the proximal catheter assembly portion 26 discussed above in connection with FIGS. 1A-2 with two cannulae 30 (or other number of cannulae) permanently attached to the bifurcation hub 16 such that each cannula extends from the distal end of the bifurcation hub, as shown in FIG. 1B. A distal catheter assembly portion is also provided, such as the distal catheter assembly portion 28 discussed above in connection with FIGS. 1A-2, including a catheter tube 12 defining two lumens (or other number of lumens) 14. The cannulae 30 are coated with the polymeric coating 38 either before or after being permanently attached to the bifurcation hub 16 using one or more of the processes described further above. As mentioned, the cannulae 30 may be bead blasted or otherwise treated to provide a relatively roughened surface prior to application of the coating 38. As described the coating 38 assists in sealing the cannulae/catheter tube interface 42 when the cannulae 30 are operably connected to the catheter tube 12, as when each cannula is received through the proximal end 12A of the catheter tube and into the corresponding lumen 14 thereof, to provide a leak-free connection. It is appreciated that other process steps can be included in the method as described while still residing within the scope of the present disclosure.

So configured, the catheter 10 can be placed in a patient via a reverse-tunneling procedure by first inserting the distal segment of the catheter tube 12, as part of the distal catheter assembly portion 26, into the vasculature of the patient so as to position the distal end 12B of the catheter tube in a desired location within the vessel. The catheter tube 12 can be trimmed by the clinician as needed, for proper length. The proximal segment of the catheter tube 12 remains external to the vessel and is then tunneled through a subcutaneous tunnel defined by the clinician until the proximal end 12A of the catheter tube extends from the tunnel.

After tunneling the proximal segment of the catheter tube 12, the proximal catheter assembly portion 28 is attached to the catheter tube via the polymer-coated cannulae 30 being received into the lumens 14 of the catheter tube through the proximal end 12A thereof. This is typically performed by the clinician manually grasping the bifurcation hub 16 and pushing the cannulae 30 into the catheter tube lumens 14 until each cannula is fully received into the corresponding lumen. This action joins the proximal catheter assembly portion 26 with the distal catheter assembly portion 28, forming a complete catheter assembly. As has been described, the intimate contact of the polymer coating of the cannulae 30 with the polymer material of the catheter tube 12 causes a knitting of the polymers, which provides a sealing effect for the cannulae/catheter tube interface 42, as desired. As will be seen, a compression component can be employed over the cannulae/catheter tube interface 42 to assist with sealing the interface. Note that, in another embodiment, the cannulae 30 need not be completely received into the lumens while still being able to provide a leak-free cannulae/catheter tube interface.

Figure 3A:
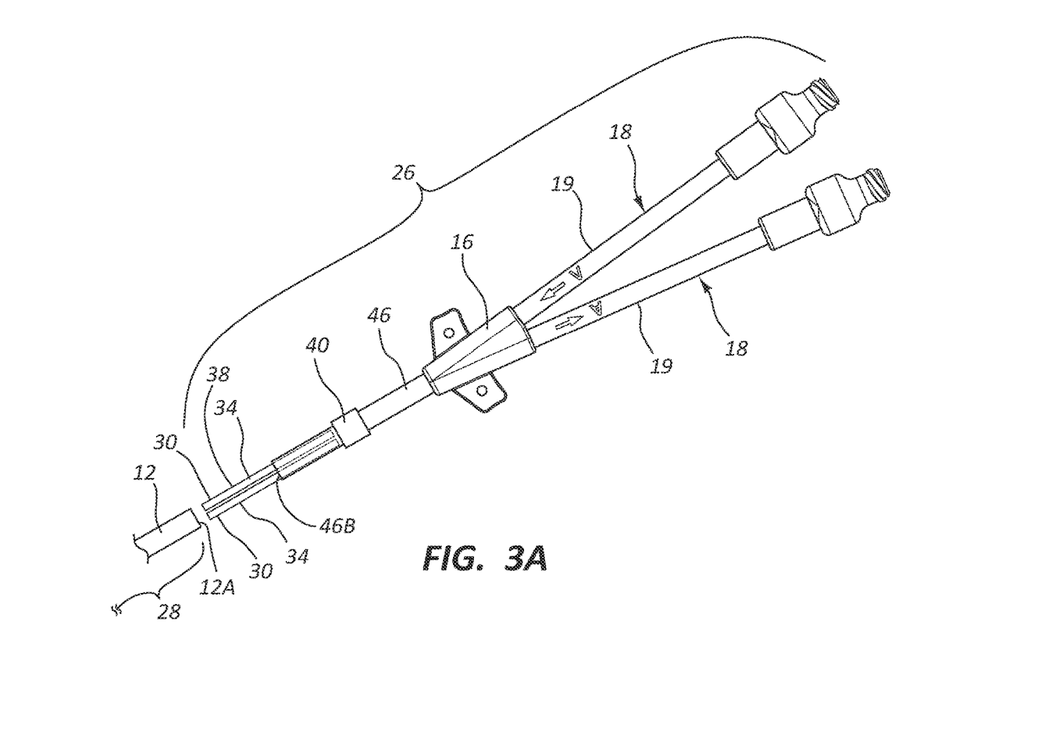
FIGS. 3A-3C depict various views of a catheter assembly according to one embodiment.
Figure 3B:
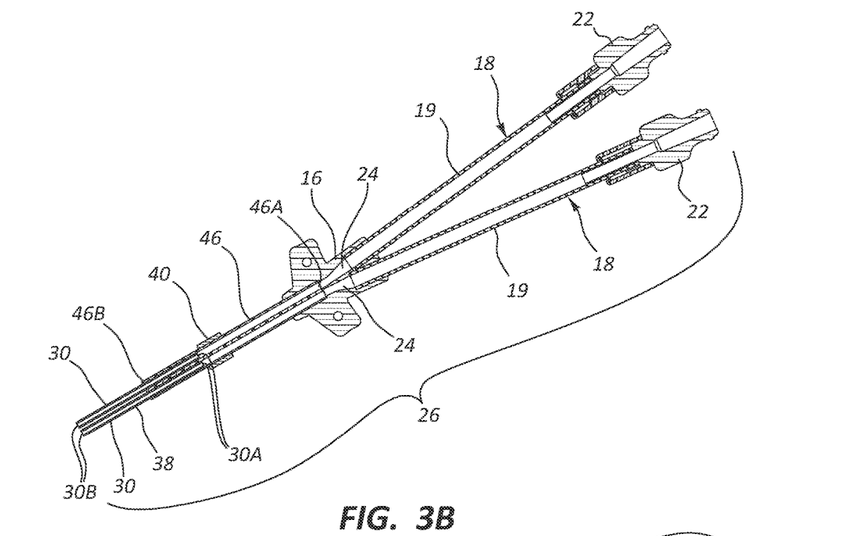
Figure 3C:
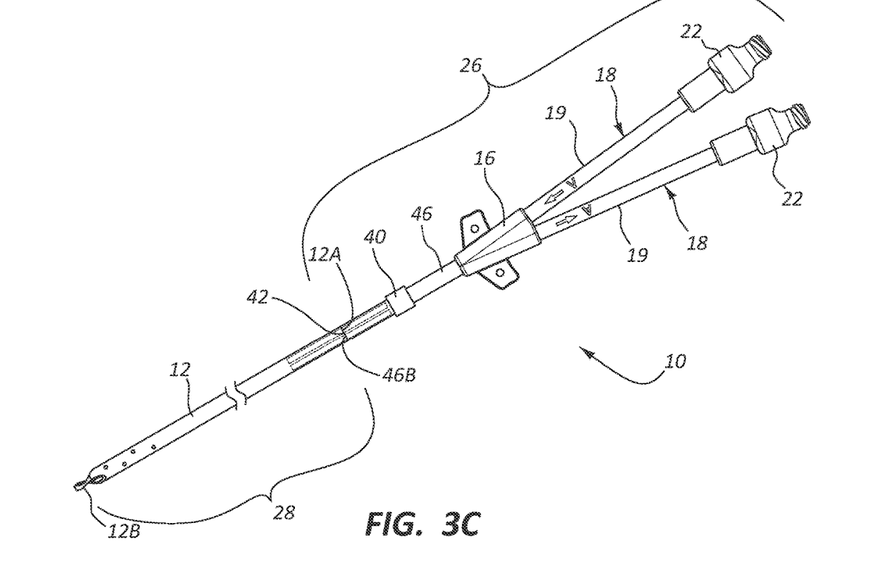

FIGS. 3A-3C depict various details of the catheter 10 according to another embodiment, wherein a proximal tube portion 46 is interposed between the bifurcation hub 16 and the cannulae 30 to form part of the proximal catheter assembly portion 26. The proximal tube portion 46 is similar in construction to the catheter tube 12 of the distal catheter assembly portion 28, defining like number and like-shaped lumens, as best seen in FIG. 3B. FIG. 3B further shows that a proximal end 46A of the proximal tube portion 46 is received within and permanently attached to the bifurcation hub 16, while the cannulae 30 extend past a distal end thereof. A securement cuff 40 is included about an exterior portion of the proximal tube portion 46.

FIG. 3C shows the catheter 10 in an assembled state and ready for use, with the proximal and distal catheter assembly portions 26, 28 joined together via the cannulae 30 at the cannulae/catheter tube interface 42. In contrast, FIG. 3A shows the catheter 10 in a dissembled state, with the proximal catheter assembly portion 26 separated from the distal catheter assembly portion 28, as it would be during a procedure to insert the catheter 10 into a vessel of a patient, for instance. Note that the cannulae/catheter tube interface 42 of FIGS. 3A-3C and the securement cuff 40 are both are positioned within the subcutaneous tunnel after joining of the proximal catheter assembly portion 26 and the distal catheter assembly portion 28 is complete. As with previous embodiments, the coating 38 on the outer surface 34 of the cannulae 30 provides a sealing effect and assists in ensuring a leak-free fit between the cannulae and the catheter tube 12.

As referred to above, FIGS. 4A-4E depict inclusion of a compression component, here a compression sleeve 50, with the catheter 10, according to one embodiment. As shown, the compression sleeve 50 includes an elongate, hollow body 52 defining a lumen 54 that extends between a proximal end 52A and a distal end 52B of the body. The compression sleeve body 52 defines a slit 56 that extends along the length thereof and through the thickness of the wall thereof. Either side of the slit 56 defines interengaging teeth 58 that enable the lumen 54 to be selectively reduced in size so as to compress the cannulae/catheter tube interface 42 when the cannulae 30 are received into the catheter tube lumens 14, as described above.

Figure 4A:
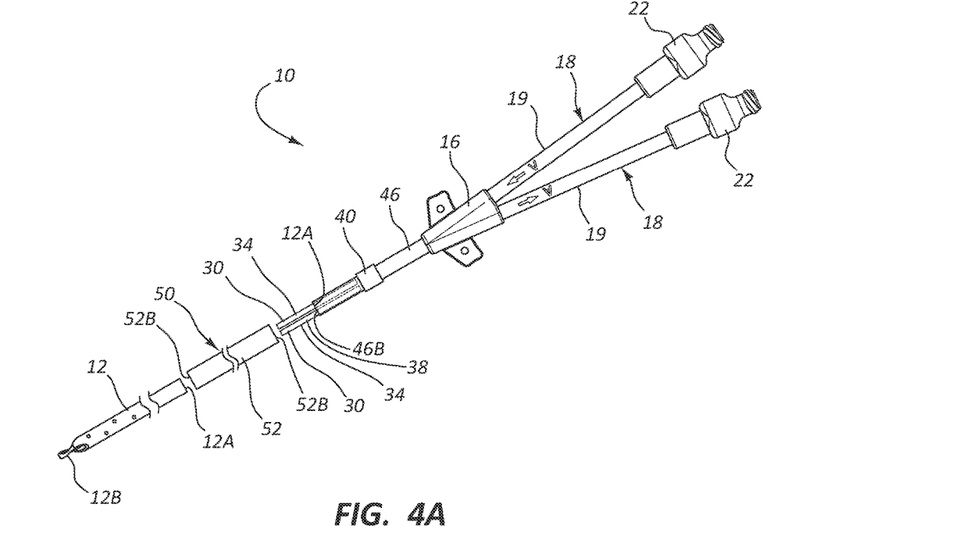
FIGS. 4A-4E depict various views of a catheter assembly according to one embodiment.
Figure 4B:
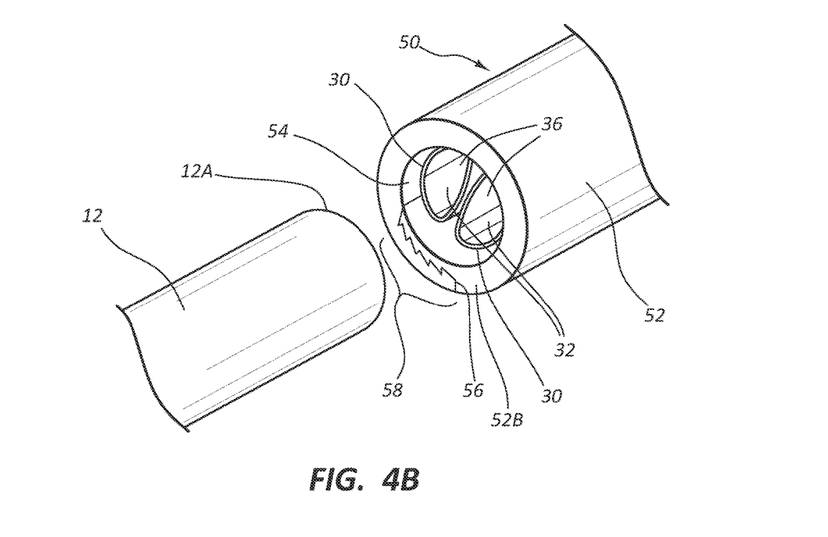
Figure 4C:
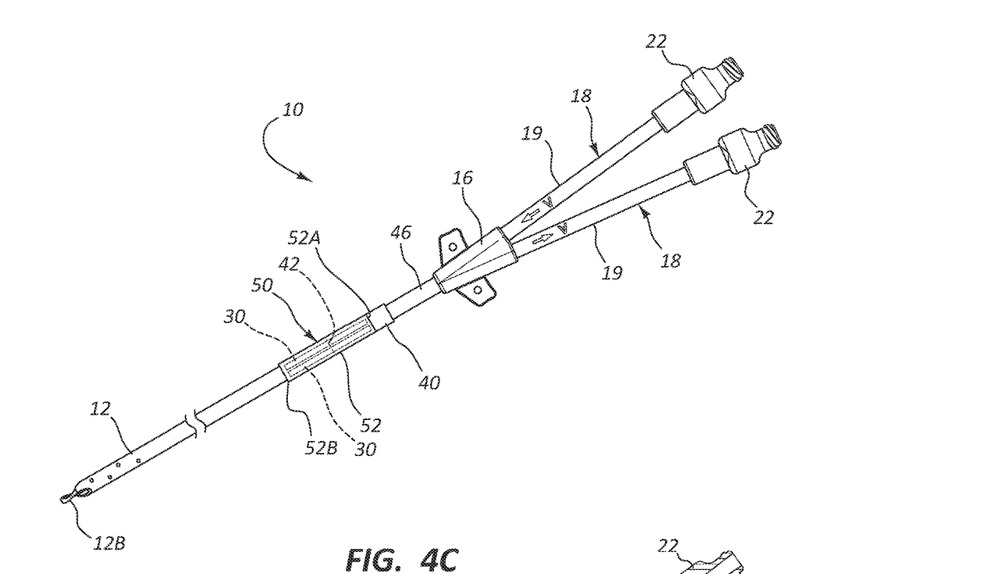

Before being compressed on to the catheter 10, the compression sleeve 50 can be slidably disposed over either the catheter tube 12 or the proximal tube portion 46. Once the cannulae 30 have been fully received into the catheter tube lumens 14 via the proximal end 12A of the catheter tube 12, the compression sleeve 50 can them be slid into place over the cannulae/catheter tube interface 42, which corresponds in the present embodiment to the junction point of the proximal end 12A of the catheter tube 12 and the distal end 46B of the proximal tube portion 46. Once the compression sleeve 50 is suitably positioned, a hemostat or other suitable device can be used to compress the sleeve body 52, by virtue of advancement of the sets of teeth 58 disposed on either side of the slit 56 past each other. This compression provides a tight fit between the outer surface 34 of the cannulae 30 and the catheter tube 12 as seen in FIG. 4C, thus assisting to prevent leaks at the cannulae/catheter tube interface 42. Of course, other suitable compression components can be employed.

Figure 4D:
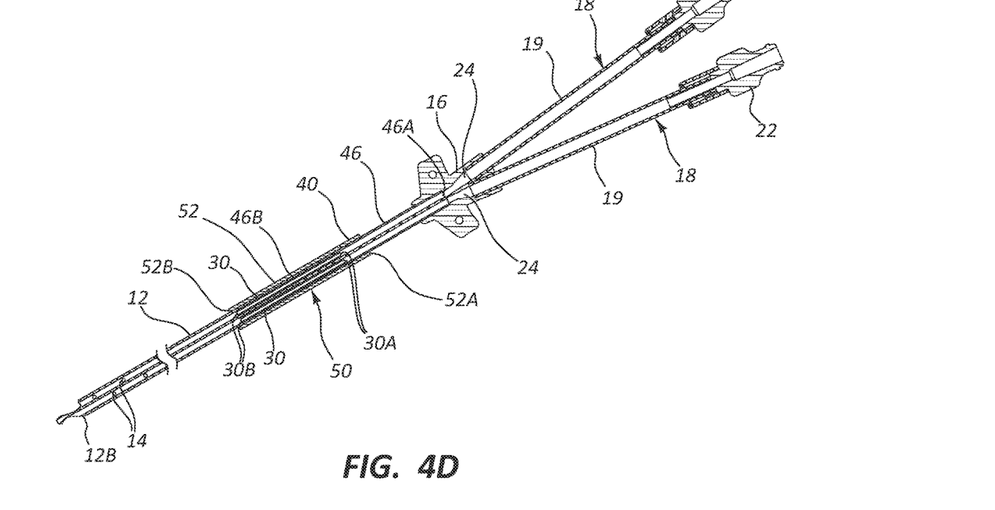
Figure 4E:
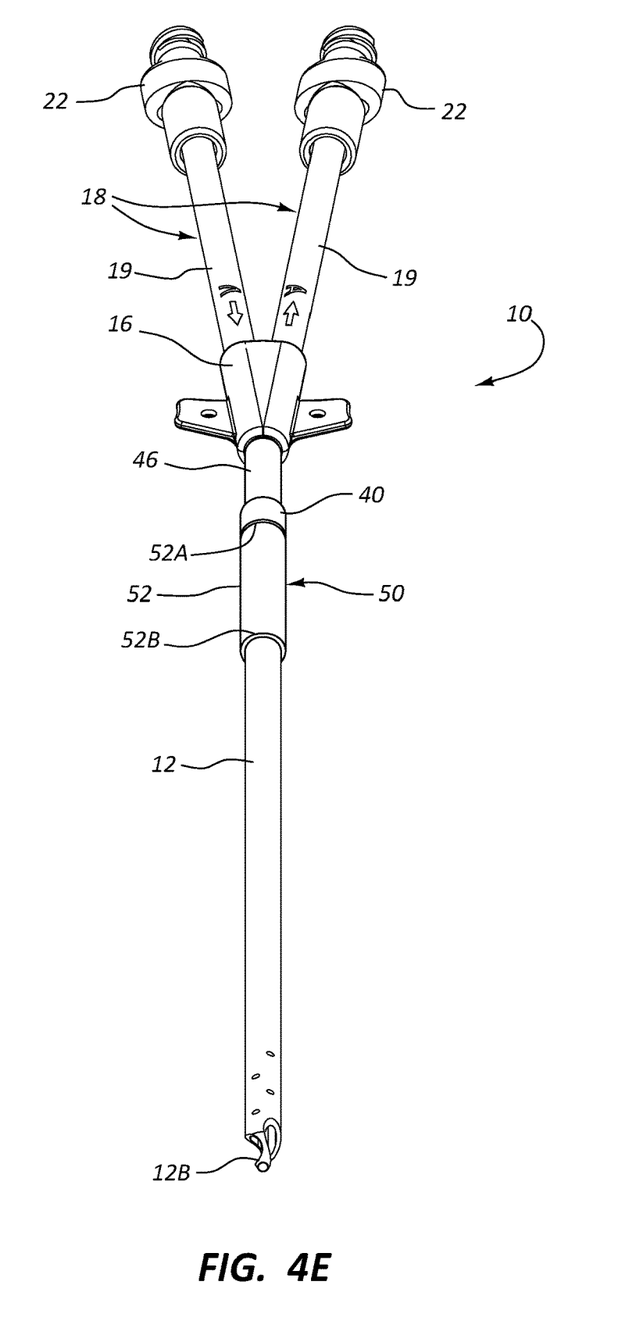
Figure 5:
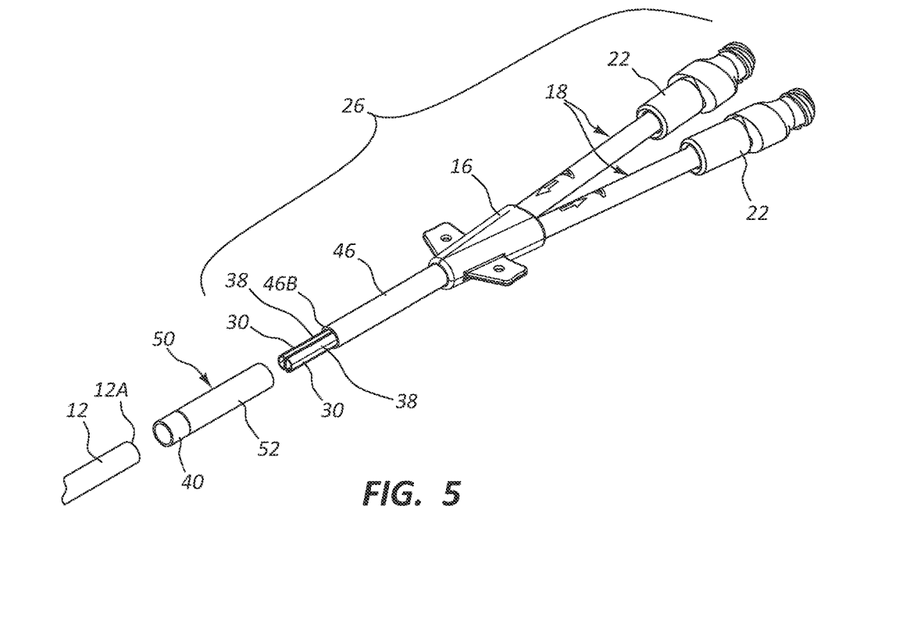
FIG. 5 is a perspective exploded view of a catheter assembly according to one embodiment.
Figure 6:
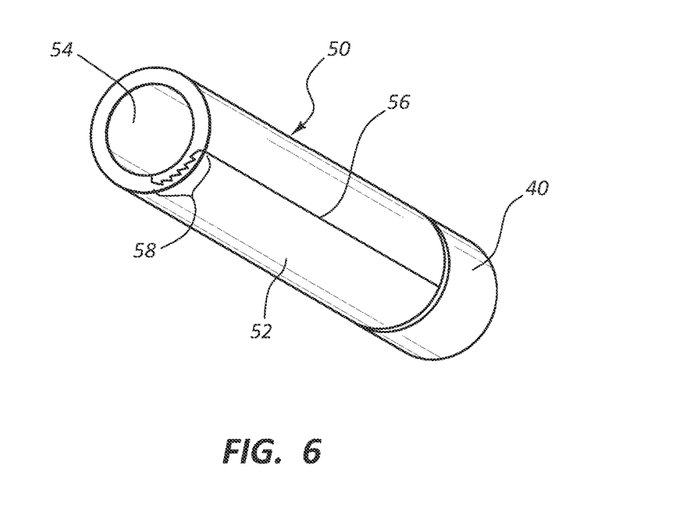
FIG. 6 is a perspective view of a compression sleeve according to one embodiment.
Figure 7A:
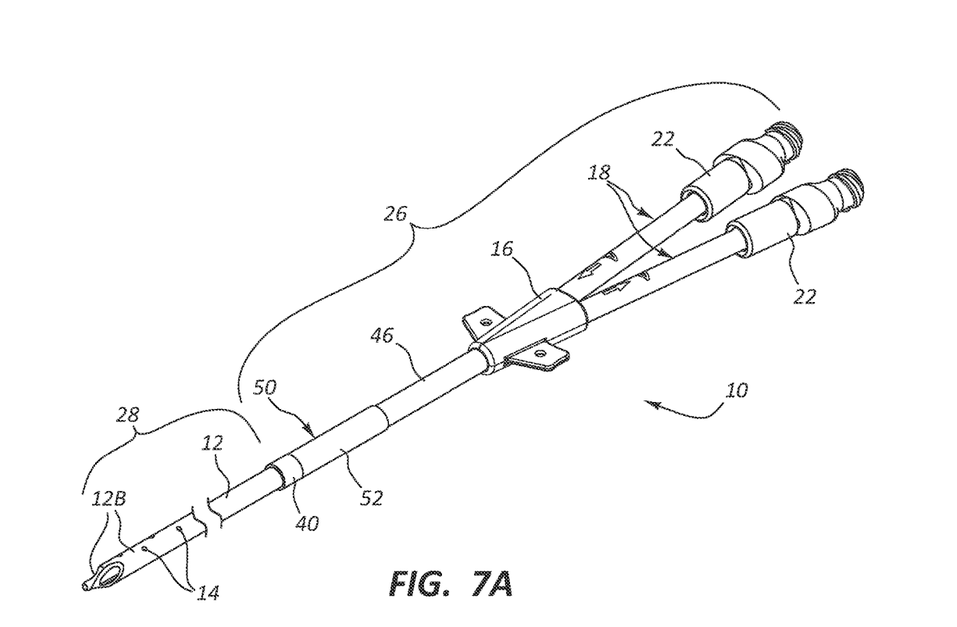
FIGS. 7A and 7B depict various views of a catheter assembly according to one embodiment.
Figure 7B:
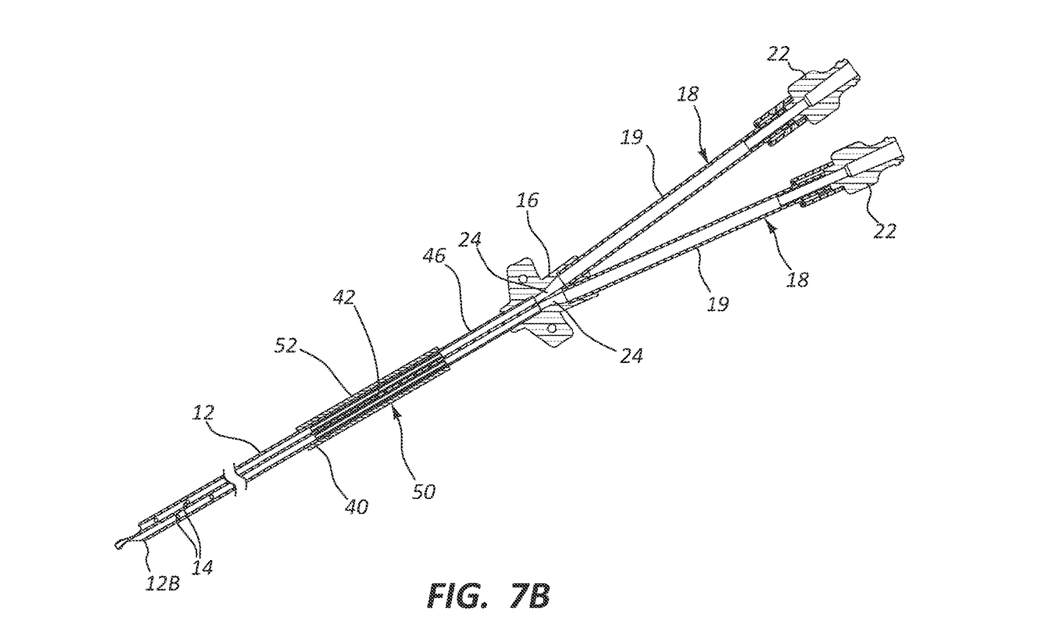

In the present embodiment, the proximal end 52A of the compression sleeve body 52 is positioned adjacent the securement cuff 40 after final placement of the compression sleeve is complete, as seen in FIGS. 4C-4E. The catheter 10 can then be retracted into the tunnel so that the compression sleeve 50 and the securement cuff 40 are disposed within the tunnel, thus protecting the cannulae/catheter tube interface 42 from potential contamination from external sources. Note that in one embodiment, the compression sleeve can be tapered in shape so as to ease passage into the tunnel. Note, that in another embodiment, heat may be applied to the cannulae/catheter tube interface 42 after joining of the proximal and distal catheter assembly portions 26, 28 in order to enhance the seal at the interface.

FIGS. 5-7B depict details of the catheter 10 according to another embodiment, wherein the securement cuff 40 is attached to the body 52 of the compression sleeve 50 itself. This, in turn, enables more flexibility in positioning the securement cuff 40 relatively more distally or more proximally, depending on the orientation of the compression sleeve 50. For instance, FIG. 7A shows the compression sleeve 50 positioned such that the securement cuff 40 attached thereto is in a distal position with respect to the remainder of the compression sleeve. In another configuration, the compression sleeve 50 can be flipped 180 degrees to position the securement cuff 40 in a proximal position with respect to the remainder of the compression sleeve, similar to the orientation shown in FIG. 6.

Note that the securement cuff in one embodiment can be positioned in any one of a variety of positions along the length of the compression sleeve and that, while permanently secured in a particular position in the present embodiment, the securement cuff in other embodiments can be initially movable along the compression sleeve until fixated in a desired position, such as via use of an adhesive.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A catheter assembly, comprising:
   a proximal catheter assembly portion including a bifurcating hub, the bifurcating hub including at least one fluid passageway;
   a distal catheter assembly portion including a catheter tube defining at least one lumen, the catheter tube including a polymeric material;
   a cannula assembly including at least one cannula operably connected with the at least one fluid passageway of the bifurcating hub, the at least one cannula further configured to operably connect with the at least one lumen of the catheter tube so as to provide fluid communication between the proximal catheter assembly portion and the distal catheter assembly portion when the proximal catheter assembly portion and the distal catheter assembly portion are connected; and
   a polymeric coating including the polymeric material, the coating included with at least one of the at least one cannula and the catheter tube, the polymeric coating configured to provide a seal between the at least one cannula and the catheter tube when the proximal catheter assembly portion and the distal catheter assembly portion are connected by an interference or slip-type fit.

2. The catheter assembly as defined in claim 1, wherein the polymeric coating is included on a surface of the at least one cannula before the proximal catheter assembly portion and the distal catheter assembly portion are connected.

3. The catheter assembly as defined in claim 2, wherein the at least one cannula is received into the at least one lumen of the catheter tube.

4. The catheter assembly as defined in claim 3, wherein the polymeric coating is included on an outer surface of the at least one cannula such that the polymeric coating is positioned adjacent a portion of an interior surface of the at least one lumen of the catheter tube when the proximal catheter assembly portion and the distal catheter assembly portion are connected.

5. The catheter assembly as defined in claim 1, wherein an interface is established when the proximal catheter assembly portion and the distal catheter assembly portion are connected, the polymeric coating configured to provide sealing to prevent fluid leakage at the interface.

6. The catheter assembly as defined in claim 5, wherein the proximal catheter assembly portion is connected to the distal catheter assembly portion after the catheter tube of the distal catheter assembly portion is subcutaneously tunneled in a patient.

7. The catheter assembly as defined in claim 6, further comprising a compression component configured to compress a region surrounding the interface.

8. The catheter assembly as defined in claim 7, wherein the compression component includes a compression sleeve and wherein the compression sleeve includes a securement cuff.

9. The catheter assembly as defined in claim 5, wherein the interface is disposed within a subcutaneous tunnel of a patient after the proximal catheter assembly portion and the distal catheter assembly portion are connected.

10. The catheter assembly as defined in claim 1, wherein the at least one fluid passageway of the bifurcating hub is operably connected to at least one extension leg.

11. The catheter assembly as defined in claim 1, wherein the polymeric material includes polyurethane.

12. The catheter assembly as defined in claim 1, wherein the polymeric material includes at least one of at least one of polyurethane, silicone, polyester, polyethyleneterephthalate, polyethylene, high density polyethylene, polyvinylchloride, low-density polyethylene, polypropylene, polystyrene, polyamides, nylons, acrylonitrilebutadiene styrene, polycarbonate, polycarbonate/acrylonitrile butadienestyrene, polyetheretherketone, and polytetrafluoroethylene.

13. The catheter assembly as defined in claim 1, wherein the at least one cannula is bead blasted prior to application of the polymeric coating.

14. The catheter assembly as defined in claim 1, wherein the at least one cannula is operably connected to the at least one fluid passageway of the bifurcating hub via a proximal tube portion interposed between the cannula assembly and the bifurcating hub.

15. The catheter assembly as defined in claim 14, wherein the proximal tube portion includes a securement cuff.

16. A catheter assembly, comprising:
a proximal catheter assembly portion including a bifurcating hub, the bifurcating hub including a plurality of fluid passageways;
a distal catheter assembly portion including a catheter tube defining a plurality of lumens, the catheter tube including a polymeric material;
a cannula assembly including a plurality of cannulae, the plurality of cannulae operably connected to corresponding fluid passageways of the bifurcating hub and the plurality of lumens of the catheter tube; each of the plurality of cannulae further configured to operably connect with a corresponding one of the plurality of lumens of the catheter tube so as to provide fluid communication between the proximal catheter assembly portion and the distal catheter assembly portion when the proximal catheter assembly portion and the distal catheter assembly portion are connected; and
a polymeric coating including the polymeric material, the coating included on a surface of the plurality of cannulae, the polymeric coating configured to provide a polymer-knitted seal with the polymeric material of the catheter tube when the proximal catheter assembly portion and the distal catheter assembly portion are connected.

17. The catheter assembly as defined in claim 16, wherein at least one of the plurality of cannulae is received into at least one lumen of the plurality of lumens of the catheter tube.

18. The catheter assembly as defined in claim 17, wherein the polymeric coating is included on an outer surface of the at least one cannula such that the polymeric coating is positioned adjacent a portion of an interior surface of the at least one lumen of the catheter tube when the proximal catheter assembly portion and the distal catheter assembly portion are connected.

19. The catheter assembly as defined in claim 16, wherein an interface is established when the proximal catheter assembly portion and the distal catheter assembly portion are connected, the polymeric coating configured to provide sealing to prevent fluid leakage at the interface.

20. The catheter assembly as defined in claim 19, wherein the proximal catheter assembly portion is connected to the distal catheter assembly portion after the catheter tube of the distal catheter assembly portion is subcutaneously tunneled in a patient.

21. The catheter assembly as defined in claim 20, further comprising a compression component configured to compress a region surrounding the interface.

22. The catheter assembly as defined in claim 16, wherein the polymeric material includes polyurethane.

23. The catheter assembly as defined in claim 16, wherein the polymeric material includes at least one of at least one of polyurethane, silicone, polyester, polyethyleneterephthalate, polyethylene, high density polyethylene, polyvinylchloride, low-density polyethylene, polypropylene, polystyrene, polyamides, nylons, acrylonitrilebutadiene styrene, polycarbonate, polycarbonate/acrylonitrile butadiene styrene, polyetheretherketone, and polytetrafluoroethylene.

24. A reverse-tunneled catheter assembly, comprising:
a proximal catheter assembly portion including a bifurcating hub with a fluid passageway;
a distal catheter assembly portion including a catheter tube of a polymeric material;
a cannula assembly including a cannula configured to fluidly connect a lumen of the catheter tube to the fluid passageway of the bifurcating hub for fluid communication between the proximal catheter assembly portion and the distal catheter assembly portion; and
a polymeric coating of the polymeric material on an outer surface of the cannula, the polymeric coating configured to provide a polymer-knitted seal between the cannula and the catheter tube when the cannula and the catheter tube are connected by an interference or slip-type fit.

25. The reverse-tunneled catheter assembly of claim 24, wherein the cannula and the catheter tube are configured to be connected after the catheter tube is tunneled in a patient in a reverse tunneling procedure.

26. The reverse-tunneled catheter assembly of claim 25, wherein the polymeric coating on the outer surface of the cannula is positioned adjacent an inner surface of the lumen of the catheter tube when the cannula and the catheter tube are connected.

27. The reverse-tunneled catheter assembly of claim 24, wherein the outer surface of the cannula includes a bead-blasted, medium coarse finish under the polymeric coating.

28. The reverse-tunneled catheter assembly of claim 24, wherein the polymeric material is selected from polyurethane, silicone, polyester, polyethyleneterephthalate, polyethylene, high density polyethylene, polyvinylchloride, low-density polyethylene, polypropylene, polystyrene, polyamides, nylons, acrylonitrilebutadiene styrene, polycarbonate, polycarbonate/acrylonitrile butadienestyrene, polyetheretherketone, and polytetrafluoroethylene.

29. The reverse-tunneled catheter assembly of claim 24, wherein the polymeric material is polyurethane.

30. The reverse-tunneled catheter assembly of claim 24, wherein the outer surface of the cannula includes a bead-blasted, medium coarse finish under the polymeric coating, the polymeric material being polyurethane such that the polymeric coating of polyurethane on the outer surface of the cannula is positioned adjacent an inner surface of the lumen of the catheter tube of polyurethane when the cannula and the catheter tube are connected after tunneling the catheter tube in a patient in a reverse tunneling procedure.

* * * * *